United States Patent [19]

Jacobson et al.

[11] Patent Number: 5,545,181

[45] Date of Patent: Aug. 13, 1996

[54] IMPLANTABLE DEFIBRILLATOR/PACER USING NEGATIVE VOLTAGE SUPPLIES

[75] Inventors: Peter Jacobson, Haguenau; Daniel Kroiss, Schweighouse-Moder; Alan Ostroff, Preuschdorf, all of France

[73] Assignee: Ela Medical, S.A., Montrouge, France

[21] Appl. No.: 320,854

[22] Filed: Oct. 11, 1994

[30] Foreign Application Priority Data

Oct. 15, 1993 [FR] France .................. 93 12265

[51] Int. Cl.$^6$ .............. A61N 1/39; A61N 1/36
[52] U.S. Cl. .................................. 607/4
[58] Field of Search .................. 607/5, 4, 6, 15, 607/16, 37

[56] References Cited

U.S. PATENT DOCUMENTS

| 27,652 | 5/1973 | Mirowski et al. | 128/419 D |
|---|---|---|---|
| 3,862,636 | 1/1975 | Bell et al. | 607/5 |
| 4,384,585 | 5/1983 | Zipes | 128/419 D |
| 4,403,612 | 9/1983 | Fogarty | 128/344 |
| 4,614,192 | 9/1986 | Imran et al. | 128/419 D |
| 4,800,883 | 1/1989 | Winstrom | 128/419 D |
| 4,989,603 | 2/1991 | Carroll et al. | 607/5 |
| 4,998,531 | 3/1991 | Bocchi et al. | 128/419 D |
| 5,002,052 | 3/1991 | Haluska | 607/5 |
| 5,111,816 | 5/1992 | Pless et al. | 128/419 D |
| 5,178,140 | 1/1993 | Ibrahim | 607/5 |
| 5,224,476 | 7/1993 | Ideker et al. | 128/419 D |
| 5,265,588 | 11/1993 | Nelson et al. | 607/5 |
| 5,372,605 | 12/1994 | Adams et al. | 607/5 |

FOREIGN PATENT DOCUMENTS

| 0281219 | 1/1988 | European Pat. Off. | A61N 1/39 |
|---|---|---|---|
| 0280526 | 2/1988 | European Pat. Off. | A61N 1/39 |
| 0326290 | 1/1989 | European Pat. Off. | A61N 1/38 |
| 0324380 | 1/1989 | European Pat. Off. | A61N 1/39 |
| 0515059 | 6/1992 | European Pat. Off. | A61N 1/39 |
| 0540266 | 10/1992 | European Pat. Off. | A61N 1/00 |
| 0551746 | 12/1992 | European Pat. Off. | A61N 1/37 |
| 0553863 | 1/1993 | European Pat. Off. | A61N 1/39 |
| 0553864 | 1/1993 | European Pat. Off. | A61N 1/39 |
| 98225A2 | 5/1994 | European Pat. Off. | 607/5 |
| 2257312 | 1/1974 | France | A61N 1/36 |
| 1149979 | 8/1983 | U.S.S.R. | A61N 1/36 |

OTHER PUBLICATIONS

Schuder J. C. et al., "Ultrahigh-energy hydrogen thyratron/SCR bidirectional waveform defibrillator", Medical & Biological Engineering & C, vol. 20, No. 4, Jul. 1982, pp. 419–424.

Schuder J. C. et al., "Transthoracic Defibrillation of 100 KG Calves With Biodirectional Truncated Exponential Shocks", vol. XXX, May 2–4, 1982, pp. 520–525.

Jones J. L. et al., "Decreased defibrillator-induced dysfunction with biphasic rectangular waveforms", American Journal of Physiology, vol. 247, Nov. 1984, pp. H793–H796.

*Primary Examiner*—George Manuel
*Assistant Examiner*—Carl H. Layno
*Attorney, Agent, or Firm*—Orrick Herrington & Sutcliffe

[57] ABSTRACT

A configuration for generating single capacitor multiphasic shocks is disclosed, using an H-bridge with four switches to connect an energy storage capacitor to a load with selectable polarity. The improvement concerns referring the negative side of the shock generator to a supply voltage which is negative with respect to pacing and sensing ground, and to connect the battery positive terminal to this same ground. This configuration permits operating the low side switches in the H-bridge, the pace/sense circuits, and the control circuitry from negative supplies derived without inversion from the negative battery terminal.

43 Claims, 1 Drawing Sheet

IMPLANTABLE DEFIBRILLATOR/PACER USING NEGATIVE VOLTAGE SUPPLIES

FIELD OF THE INVENTION AND DEFINITIONS

The present invention relates to circuitry for delivering high energy shocks in an implantable defibrillator, and more particularly to circuitry for delivering monophasic or multiphasic truncated shocks to a load from a single capacitor, and to the connection of this circuitry to the rest of the implanted defibrillator.

As used herein, the term "defibrillator" refers to any device intended to revert a tachyarrhythmia with electrical energy substantially exceeding the energy typically provided by implantable cardiac stimulators (pacemakers) to stimulate a heartbeat, including any combination or subset of implantable defibrillators, cardioverters, and pacemakers. Further, as used in the specification, a "monophasic shock" delivers current in one direction; a "multiphasic shock" delivers current first in one direction (called the first phase of the shock) and then in the opposite direction (called the second phase), and may provide additional phases which are typically of alternating polarity; a "biphasic shock" provides two phases; a "truncated shock" abruptly stops delivering current to the load, either by interrupting the current in the load or by rapidly discharging the storage capacitor; the "load" represents the impedance of lead wires, defibrillation electrodes, the electrode-tissue interface, and tissue bulk between the electrodes; a "single capacitor" and a "capacitor" each refer to one capacitor and/or any series and/or parallel combination of capacitor packages which results in a single equivalent capacitor with two terminals connected to the shock circuit; and a "battery" can be a single battery or multiple batteries arranged in parallel or in series or in some combination of both.

The cardiac stimulation voltage is negative relating to the ground potential. In its delivery, the ground potential is connected to a large indifferent electrode, and the relatively negative stimulation voltages delivered at a smaller stimulating electrode. This avoids anodic stimulation and undesired induced arrythmias.

The present invention pertains to circuits to generate single-capacitor multiphasic waveforms, and does not pertain to circuits to generate multiple-capacitor multiphasic waveforms. As noted, the single-capacitor waveform discharges the capacitor through the load in a first direction in the first phase, interrupts the current, and discharges the capacitor still further through the load in the opposite direction in the second phase, and then truncates. As a consequence, the second phase leading edge amplitude typically equals first phase trailing edge amplitude. The multiple-capacitor waveform, on the other hand discharges a different single capacitor for each direction, or even for each phase, so that the leading edge amplitude does not necessarily depend on trailing edge amplitude of the preceding phase.

BACKGROUND OF THE INVENTION

Early defibrillators provided only monophasic waveforms. USRE27652 to Mirowski (priority 09 Feb. 1970) refers to an automatic defibrillator with a monophasic shock circuit which delivered an untruncated shock as soon as the storage capacitor charged to a fixed voltage. FR2257312 to Zacouto (priority 16 Jan. 1974) refers to providing sequential monophasic shocks over multiple electrode pairs. U.S. Pat. No. 4,403,614 to Engle (priority 19 Jul. 1979) and U.S. Pat. No. 4,384,585 to Zipes (priority 06 Mar. 1981) refer to synchronizing shock with detected events, but do not show any details of the discharge circuits. U.S. Pat. No. 4,614,192 to Imran (priority 21 Apr. 1982) refers to truncating monophasic shocks by rapidly discharging the storage capacitor.

Following experiments with bidirectional shocks in 1964 and 1980, J. C. Schuder et.al. described an "Ultrahighenergy thyratron/SCR bidirectional waveform defibrillator", in Med Biol Eng Comput 20:419, 1982, referring to a biphasic generator with one capacitor per phase. SU1149979 to Pekarski (priority 08 Oct. 1983) also referred to a biphasic truncated shock circuit with one capacitor for each phase.

In 1984, Schuder et al. presented results of a simulated single-capacitor truncated biphasic waveform. In their paper entitled "Transthoracic Defibrillation of 100 Kg Calves with Bidirectional Truncated Exponential Shocks", Vol XXX Trans Am Soc Artif Intern Organs, 1984, the authors disclosed experiments made with an "asymmetrical truncated exponential biphasic waveform . . . which can be implemented in a clinical sized apparatus." They showed a waveform where the trailing edge of the first phase was equal to the leading edge of the second phase.

The single capacitor approach simplifies both charging and discharging circuits, reducing size, weight, and unreliability in implantable devices. As data accumulated showing improved animal and clinical results with biphasic truncated shocks, compared to monophasic truncated shocks, a variety of single capacitor multiphasic truncated waveform generators were proposed. All such circuits include at least four switches in an H-bridge configuration (herein also called an "H-bridge switch").

Designers frequently employ the H-bridge configuration for driving a load in two directions from a DC source, for example, driving a stepper or servo-motor from a battery. In the first phase, a first switch connects the positive source pole to a first side of the load and a second switch connects the negative source pole to the second side of the load. In the second phase a third switch connects the positive source pole to the second side of the load, and a fourth switch connects the negative source pole to the first side of the load. The first and third switches, connected to the positive source pole, are called high side switches. The second and fourth switches, connected to the negative source pole, are called low side switches. Prior art implantable discharge circuits employ one or more of three types of switches in the H-bridge. Each type of switch has an input, output, and control terminal, and responds to a control signal between the control and output terminals. Silicon controlled rectifiers (SCRs) or thyristors turn on in response to a pulse on the control terminal, but only turn off when current through them falls essentially to zero. Metal-oxide-semiconductor field effect transistors (MOSFETs) and insulated-gate bipolar transistors (IGBTs) remain on while a control voltage appears at the control terminal.

Depending on how they protect pacing and sensing circuits from defibrillation pulses, prior art circuits either isolate the capacitor and discharge circuit from pacing (stimulation) and sensing (detection) ground, or they connect the negative side of the capacitor to ground. In the isolated version they must provide isolated switch control signals. In the negative-ground version, they must still provide isolated control signals to the high side switches. Thus any single capacitor biphasic shock circuit has two high side switches and two low side switches connected in an H-bridge, and at least two isolated switch drivers. The following prior art patents all disclose an H-bridge for generating a single-capacitor multiphasic waveform, where the structure for the switch means and the switch control means differ in each design.

U.S. Pat. No. 4,800,883 to Winstrom (priority 02 Apr. 1986) provided an isolated discharge circuit with four MOSFET switches, and used a transformer with an RF carrier, rectification, and rapid shutoff circuits for high and low side drivers. A single transformer with two secondaries drove both high and low side switches in the same phase. A multilevel capacitor with voltage taps was shown.

EP0281219 to Mehra (priority 14 Jan. 1987) provided a negative-ground discharge circuit with an SCR in series with a MOSFET for each high side switch, and an SCR for each low side switch. Mehra did not give details of the switch drivers.

EP0280526 to Baker (priority 27 Feb. 1987) used the Winstrom circuit above, with the additional requirement of a first phase duration longer than the second phase duration (note that in 1984 Jones et al. published results for defibrillation pulses with 5 ms first phase and 1 ms second phase, see Am. J. Physiol. 247 (Heart Circ. Physiol. 16)). Baker also showed protection against short-circuited load, which opened the H-bridge switches when load current exceeded a preset value.

EP0324380 to Bach (priority 12 Jan. 1988) provided another negative-ground discharge circuit, with SCRs for high side switches and MOSFETs for low side switches. Bach used pulse transformers for high side drivers and drove the low side directly. Bach included diodes in series with low side switches to protect against external defibrillators (the SCRs in the high side will not pass reverse current).

EP0326290 to de Coriolis (priority 19 Jan. 1988) provided yet another negative-ground discharge circuit, with two SCRs in series for the first phase high side switch, a MOSFET for the first phase low side switch, and SCRs for the second phase high and low side switches. de Coriolis truncated the second phase by rapidly discharging the storage capacitor through the first phase high side switch and the second phase low side switch. de Coriolis drove the high side switches with pulse transformers and the low side switches with level shifters referred to a positive supply.

U.S. Pat. No. 4,998,531 to Bocchi (priority 28 Mar. 1990) provided still another negative-ground discharge circuit, with four MOSFET switches. Each MOSFET switch had a series diode to prevent reverse current during external defibrillation. Bocchi used level shifters for low side drivers and used a transformer for each high side driver, where a pulse in one direction turned the MOSFET on and a pulse in the other direction turned it off.

U.S. Pat. No. 5,111,816 to Pless (priority 22 Oct. 1990) provided yet another negative-ground discharge circuit, with IGBT or MOSFET switches. All Pless variants drive both high and low side switches in the same phase from a common transformer with an RF carrier and rectification, and a rapid shutoff circuit for at least one switch in each phase. Pless also referred the negative battery terminal to ground and inverted this to make the pacing voltage.

All prior art designs either isolate the discharge circuit from pacing and sensing ground, or refer the negative pole of the storage capacitor to pacing and sensing ground. This requires making a positive supply for the low side switch drivers and a negative supply for pacing and sensing. It also requires supplying control circuitry from either the positive or negative supply, and then translating control signals for either pacing and sensing or shock control. Hence, there is room for improvement in single capacitor multiphasic truncated shock generators.

OBJECTS AND SUMMARY OF THE INVENTION

It is, therefore, an object of this invention to simplify the power supply circuitry and the control circuitry for the discharge circuit in an implantable pacemaker/defibrillator.

It is a further object of this invention to operate pacing, sensing, control logic, and low side shock switch control in a voltage range which is negative with respect to the cardiac pacing and sensing ground.

It is still another object of this invention to derive all power supplies for pacing, sensing, control logic, and low side shock switch control from a battery supply without inversion. Such single-sided configurations are more easily amenable to implementation on an integrated circuit.

In accordance with the present invention, to accomplish the foregoing objectives, a circuit structure and function is disclosed in which the battery positive terminal is connected to ground, and the low side of the shock delivery circuit H-bridge switch and the shock storage capacitor are connected to a negative voltage supply with respect to ground. Accordingly, the present invention operates the control circuitry between a first negative voltage and ground, operates the pace/sense circuitry between a second negative voltage and ground, and operates the low side shock switch control between a third negative voltage and ground, where the third negative voltage is the one which connects to the low side of the H-bridge switch of the shock discharge circuit.

In accordance with the invention, the three negative voltage supplies may be derived from the battery in any number of different manners.

One aspect of the invention is directed to a shock circuit for use in an implantable cardiac pacemaker having a defibrillator function, (also referred to herein as a defibrillator), which includes a multiphasic shock generator for delivering bi- or multi-phasic shock waveforms from a single-capacitor structure.

A typical multiphasic shock generator includes a battery for supplying energy, control circuits for timing pacing and shock events (i.e., the time and duration of the pacing pulses and the shock phases), pace/sense circuits for providing pacing (stimulation) pulses and sensing heartbeats (detection), a shock charging circuit for converting battery energy to shock energy, a capacitor for storing shock energy, and a shock circuit for delivering the shock with selected polarity between the two poles of an H-bridge switch. A suitable shock circuit includes two high side electronic switches and two low side electronic switches in the H-bridge switch configuration for connecting the capacitor with a selected polarity to a load, i.e., cardiac tissue, two isolated high side drivers for selectively operating each high side switch in response to a corresponding signal from said control circuits, two low side drivers for selectively operating each low side switch means in response to a corresponding signal from said control circuits, and a circuit supplying power from said battery to said control circuits, pace/sense circuits, and low side drivers.

In accordance with the present invention, the foregoing shock circuit includes a connection, from the positive terminal of said battery, to ground, a first negative supply voltage for powering said control circuit between said first negative supply voltage and ground, a second negative supply voltage for powering said pace/sense circuit between said second negative supply voltage and ground, a third negative supply voltage for powering said low side drivers between said third negative supply voltage and ground, and a connection, from said third negative supply voltage, to the negative terminal of said capacitor and H-bridge switch of the shock circuit.

In one embodiment, the first, second and third negative supply voltages are produced by respective first, second and third circuit means for deriving the negative supply voltage. One such circuit means for deriving the first negative supply voltage is a direct connection to the battery negative terminal. Alternatively, the means for deriving a first negative supply voltage may include a voltage regulator circuit for stabilizing the battery voltage. The first negative supply voltage is preferably between approximately −1.0 and −3.0 V.

Similarly, a circuit means for deriving the second negative supply voltage may include a direct connection to the battery negative terminal. Alternatively, the means for deriving the second negative supply voltage is a direct connection to the first negative supply voltage. Preferably, the means for deriving the second negative supply voltage includes a voltage regulator circuit for stabilizing the battery voltage. In yet another alternative, the means for deriving the second negative supply voltage includes a voltage multiplier circuit operating from said first negative supply voltage. Preferably, the second negative supply voltage is between approximately −0.5 and −10 V. The second negative supply voltage is more preferably a programmable value, where programming is conducted in a conventional manner for implantable cardiac devices.

In one embodiment of the invention, the means for deriving the third negative supply voltage for powering said low side drivers is a direct connection to the battery negative terminal. Alternately, the means for deriving the third negative supply voltage is a direct connection from said first negative supply voltage. Preferably, the means for deriving the third negative supply voltage includes a voltage regulator circuit for stabilizing the battery voltage. In yet another embodiment, the means for deriving the third negative supply voltage is a voltage multiplier circuit operating from said first negative supply voltage. The third negative supply voltage is preferably between approximately −10 and −15 V.

The pacemaker/defibrillator of the present invention further includes a resistor interposed between the third negative supply voltage and the negative terminal (low side) of the H-bridge switch of the shock circuit. This resistor is used as a sensing resistor for monitoring the shock energy, and may be divided down across a resistor network so that the control circuits can directly measure the shock current based on the voltage drop across the sensing resistor. A suitable resistance has been found to be 0.03 ohms.

BRIEF DESCRIPTION OF THE DRAWING

Further features of the invention, its nature and various advantages will be apparent from the accompanying drawing and the following detailed description of the invention, in which the figure shows an electrical circuit schematic of a shock circuit in accordance with a preferred embodiment of the invention, applied to an implantable pacemaker/defibrillator.

DETAILED DESCRIPTION OF THE INVENTION

Figure 1:
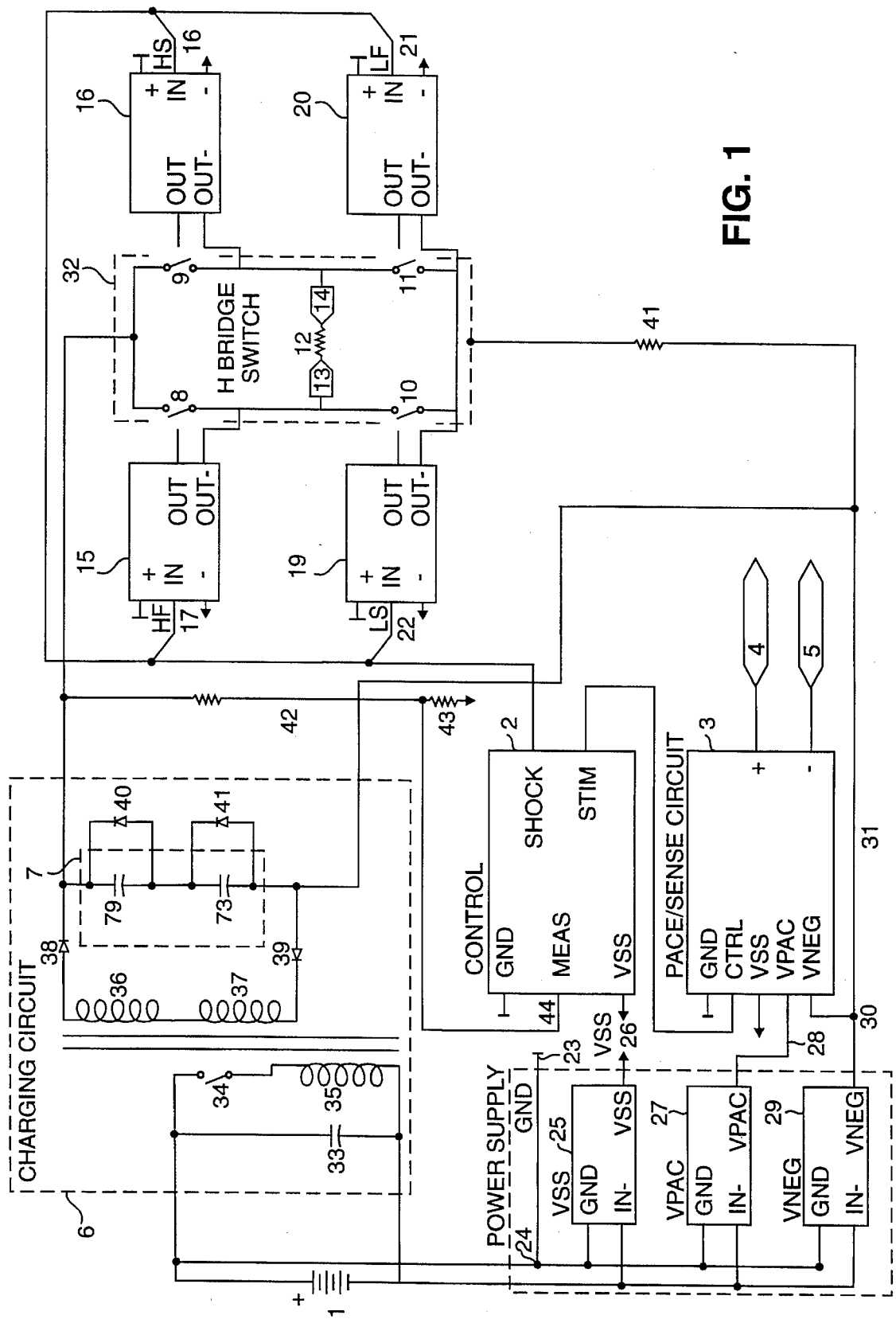

Referring to the Figure, a battery 1 supplies energy to all device circuits. Control circuits 2 time pacing and shock events. Pace/sense circuits 3 provide pacing (stimulation) pulses and sense heartbeats (detection), at electrode terminals 4 and 5. The Figure also shows a shock charging circuit 6 for converting battery energy to shock energy, including a capacitor 7 comprised of individual capacitors 7A, 7B for storing shock energy.

The figure also shows two high side electronic switches 8 and 9, and two low side electronic switches 10 and 11, in an H-bridge switch configuration 32, for connecting said capacitor 7 (including capacitors 7A, 7B), with selective polarity to a load 12. Load 12 is connected between shock electrode terminals 13 and 14 in the H-bridge switch 32. The Figure shows two isolated high side drivers 15 and 16 for selectively operating each high side switch in response to a corresponding signal HF at 17 and HS at 18 from said control circuits 2.

The circuit also has two low side drivers 19 and 20 for selectively operating each low side switch 10 and 11 in response to corresponding signals LF at 21 and LS at 22 from said control circuits 2.

The Figure also shows a power supply circuit 23 for supplying power from battery 1 to control circuits 2, pace/sense circuits 3, and low side drivers 19 and 20. Power supply 23 includes:

A connection 24 from the positive terminal of battery 1 to ground,

A VSS supply circuit 25 for deriving a first negative supply voltage called VSS at 26 for powering control circuits 2 between VSS and ground, for serving as a logic reference level throughout the device, and for powering high side drivers 15 and 16, A VPAC supply circuit 27 for deriving a second negative supply voltage called VPAC at 28 for powering pace/sense circuits 3 between VPAC and ground, A VNEG supply circuit 29 for deriving a third negative supply voltage called VNEG at 30, for powering low side drivers 19 and 20 between VNEG and ground, and A connection 31 from VNEG, to the negative terminal of single capacitor 7A, 7B and to the shock circuit 32 via optional sensing resistor 41. The value of resistor 41 is very low, approximately 0.03 Ohms, and there is essentially zero voltage across it during normal operation of the circuit.

Preferably, in the power supply 23: VSS at 26 is approximately 1.0 to −3.0 V, VPAC at 28 is approximately −0.5 to −10 V, the value of which is optionally programmable, and VNEG at 30 is approximately −10 to −15 V.

Numerous alternate configurations of power supply 23 and its component circuits for providing the first (VSS), second (VPAC) and third (VNEG) negative supply voltages, and their constructions, exist within the scope of the invention and the abilities of a person of ordinary skill in the art. The Figure shows one such configuration having three separate regulated supplies 25, 27, and 29, each operating directly from the battery. Examples of alternative configurations include: (1) connecting one or more of the supply outputs directly to the battery negative terminal without regulation, (2) connecting one or more of the supply outputs to a single regulator, or (3) deriving second and third voltages from the battery and/or the first regulated voltage, using, for example, voltage multipliers or level shifters.

Referring still to the Figure, pace/sense circuits 3 include logic operating between ground and VSS, and pacing signal generation (i.e., the stimulation pulse) operating between ground and VPAC. The circuits 3 may also use VNEG which is always at least as negative as VPAC, to provide a common mode operating region including VPAC.

The charging circuit 6 converts battery voltage to high voltage for shocks. Charging circuit 6 input connects across the battery 1, and is filtered with capacitor 33. Charging circuit 6 output connects across H-bridge switch 32. Very briefly, when switch 34 closes, current ramps up in transformer primary 35. When switch 34 opens, current starts to flow through transformer secondaries 36 and 37, charging shock capacitor 7 through diodes 38 and 39. In the illustration of the principles of the invention in the Figure, capacitor 7 is made of two capacitors 7A, 7B in series. Numerous other configurations, including one capacitor, or other series and parallel combinations, could also be used within the scope of the invention. The charging circuit 6 charges capacitor 7 (i.e., capacitors 7A and 7B) to a preset voltage determined by regulating means not shown here, but which are well known, and shown in numerous examples, in the prior art. One useful charging circuit is disclosed in copending and commonly assigned U.S. patent application Ser. No. 08/287,834, filed Aug. 9, 1994 in the name of Peter Jacobson, the disclosure of which is incorporated herein by reference.

When control circuits 2 assert HF at 17 and LF at 21, high side driver 15 and low side driver 20 convey these control signals to close switches 8 and 11 respectively, so that current flows from capacitor 7 through load 12 in a first direction, from 13 to 14 (this is the first shock phase). Then, low voltage circuits 2 de-assert all control outputs 17, 18, 21, 22, opening all switches. This provides a delay between phases, giving time for all of the switches to open. Next, low voltage control circuits 2 assert HS at 18 and LS at 22, so that high side driver 6 and low side driver 19 close switches 9 and 10 respectively. As a result, current flows from capacitor 7 through load 12 in a second direction, from 14 to 13 (this is the second shock phase). Then, low voltage circuits 2 de-asserts all control outputs 17, 8, 21, and 22. This opens all switches and truncates the second phase. The low voltage circuits 2 can optionally continue this sequence to generate additional phases.

Switches 8 to 11 can be implemented as MOSFETs, IGBTs, or SCRs, as familiar to designers skilled in the art. Since SCRs cannot be turned off until current through them falls to zero, they can only be used in either the high or low side switch for one phase, but not in both sides in the same phase. MOSFETs or IGBTs should have series diodes as shown in prior art, to prevent external defibrillation from being conducted in the opposite direction through the switches.

Low side switch drivers 19 and 20 translate a logic level signal between VSS and GND to a more negative signal between VNEG and GND. Examples are shown in the prior art cited above. High side switch drivers 15 and 16 translate a logic level signal between VSS and GND to provide an isolated control signal output. Examples using pulse transformers for SCR switches, or RF transformers for MOSFET or IGBT switches, are well known and shown in the prior art cited above.

Resistor 41 obtains a further advantage of the circuit of the invention as compared to prior known isolated output circuits. During a shock the voltage across resistor 41 depends directly on the shock current. When shock current flows, the side of resistor 41 connected to low side drivers 19 and 20 becomes positive with respect to VNEG. Thus circuits (not shown) operating between VDD and VNEG, could be used to measure shock current during shock.

It also may be useful to include means to measure high voltage output of the charging circuit 6. A voltage divider consisting of resistors 42 and 43 is used in the example shown to scale the high voltage output of the charging circuit to a low voltage referred to VSS. If the divider ratio is selected correctly, at 1000:1, for example, then the voltage at the junction 44 of resistors 42 and 43 remains between VDD and VSS, and is convenient for control circuits 2 to measure at input 44.

In this regard, the voltage divider (resistors 42 and 43) has a reference signal VSS that is the first negative voltage supply 26. The voltage at the node between resistors 42 and 43, called the voltage divider output, with respect to the reference supply VSS, corresponds in almost direct proportion to the voltage stored on the capacitor 7. (The error of this approximation becomes small when the voltage across the capacitor 7 greatly exceeds the negative power supply voltages, as in the case of defibrillation shocks.)

The energy stored in capacitor 7 also is approximately dependent on the square of the capacitor voltage. Thus, by measuring the voltage divider output before and after delivery of a shock, a difference of the square of those two voltages can be determined, which difference corresponds approximately linearly to the energy discharged during said shock. This voltage sampling and calculation can be implemented, for example, in a software program controlling the control circuits 2, or by addition of hardware circuits, which implementations are within the ability of a person of ordinary skill in the art.

A further advantage of referring the shock circuit to a negative supply VNEG, rather than to ground, becomes evident considering that: (a) charging circuit 6 charges and holds the voltage across capacitor 7 at a constant value as explained earlier; (b) VSS supply 25 charges VSS to a constant voltage; and (c) the current in resistors 42 and 43 tend pull the top of capacitor 7 toward ground when it is charged. Since capacitor 7 has a constant voltage across it, this pushes the bottom of capacitor 7 further negative, providing an additional mechanism for charging negative supply VNEG when capacitor 7 is charged. When capacitor 7 is charged, this means that the defibrillator is armed to deliver a shock. At this moment it is important to have a high voltage difference between VDD and VNEG, to provide maximum gate drive to the low side drivers 19 and 20. Referring the shock circuit to a negative supply thus provides additional charging current for that negative supply, just at the time when it is most needed.

Although the invention has been described with reference to particular embodiments, it is to be understood that these embodiments are merely illustrative of the application of the principles of the invention, and not limiting. Numerous other modifications may be made and other arrangements may be devised by persons of ordinary skill in the art without departing from the spirit and scope of the present invention.

We claim:

1. A multiphasic defibrillator shock generator for an implantable device, comprising:

a battery to supply energy, having a positive and a negative terminal;

control circuits having a supply input and output control signals to control pacing and shock events;

a pace circuit to provide pacing pulses to the heart in response to a first output control signal, the pace circuit having a supply input;

a shock charging circuit coupled to the battery and operable to convert battery energy to shock energy, the shock charging circuit having an output;

a capacitor coupled to the shock charging circuit output to store shock energy, having a positive terminal and a negative terminal;

two high side electronic switches and two low side electronic switches connected in an H-bridge switch configuration, the H-bridge switch being coupled to said capacitor to connect said capacitor with selective polarity to a load, the H-bridge switch configuration having a positive terminal coupled to the capacitor positive terminal, a negative terminal coupled to the capacitor negative terminal, and two shock electrodes located respectively between the high and low side switches;

two isolated high side drivers selectively operating each high side switch in response to a corresponding output control signal from said control circuits;

two low side drivers for selectively operating each low side switch in response to a corresponding output control signal from said control circuits; and a circuit supplying power from said battery to said control circuit, pace circuit, and low side drivers, wherein the improvement comprises:

a connection from the positive terminal of said battery to a ground;

first means for deriving a first negative supply voltage, the first negative supply being input to said control circuit supply input wherein said control circuit operates between said first negative supply voltage and ground;

second means for deriving a second negative supply voltage, the second negative supply being input to said pace circuit supply input wherein said pace circuit operates between said second supply voltage and ground;

third means for deriving a third negative supply voltage, the third negative supply voltage being input to the low side drivers input wherein said low side drivers operate between said third negative supply voltage and ground; and a connection from said third negative supply voltage to the negative terminal of said capacitor and H-bridge switch.

2. The apparatus of claim 1 wherein said first deriving means comprises a direct connection to the battery negative terminal.

3. The apparatus of claim 1 where said first deriving means comprises a voltage regulator circuit.

4. The apparatus of claim 3 where said first negative supply voltage is regulated between approximately −1.0 and −3.0 V.

5. The apparatus of claim 1 where said second deriving means comprises a direct connection to the battery negative terminal.

6. The apparatus of claim 1 where said second deriving means comprises a direct connection to said first negative supply voltage.

7. The apparatus of claim 1 where said second deriving means comprises a voltage regulator circuit.

8. The apparatus of claim 7 where said second negative supply voltage is regulated between approximately −0.5 and −10 V.

9. The apparatus of claim 1 where said second deriving means comprises a voltage multiplier circuit operating from said first negative supply voltage.

10. The apparatus of claim 9 where said second negative supply voltage is between approximately −0.5 and −10 V.

11. The apparatus of claim 4 where said second negative supply voltage is a programmable value selected from between −0.5 and −10.0 V.

12. The apparatus of claim 1 where said third deriving means comprises a direct connection to the battery negative terminal.

13. The apparatus of claim 1 where said third deriving means comprises a direct connection to said first negative supply voltage.

14. The apparatus of claim 1 where said third deriving means comprises a voltage regulator circuit.

15. The apparatus of claim 14 where said third negative supply voltage is regulated at a voltage between approximately −10 and −15 V.

16. The apparatus of claim 1 where said third deriving means comprises a voltage multiplier circuit operating from said first negative supply voltage.

17. The apparatus of claim 16 where said third negative supply voltage is between approximately −10 and −15 V.

18. The apparatus of claim 1 further comprising a resistor connected between said third negative voltage supply and the negative terminal of said H-bridge switch.

19. The apparatus of claim 18 wherein said resistor has a value of approximately 0.03 ohms.

20. The apparatus of claim 1 further comprising a voltage divider circuit connected to an output of the capacitor having an output signal corresponding to a fraction of the capacitor output.

21. The apparatus of claim 20 wherein the control circuit further comprises an input to receive the voltage divider circuit output.

22. An implantable multiphasic defibrillator-shock generator comprising:

a ground;

an energy storage battery having a positive terminal and a negative terminal, the battery positive terminal being connected to ground;

a power supply connected to said battery having a first negative supply voltage, a second negative supply voltage, and a third negative supply voltage;

a capacitor to store shock energy and to discharge stored energy as a shock into a load, the capacitor having a positive terminal and a negative terminal;

a shock charging circuit having an input coupled to the positive and negative terminals of the battery and an output coupled to the positive and negative terminals of the capacitor, the shock charging circuit being operable to store battery energy in the capacitor;

a shock delivery circuit comprising two high side switches having corresponding high side drivers and two low side switches having corresponding low side drivers, the high side switches and low side switches being connected in an H-bridge switch configuration having a negative terminal and a positive terminal, the negative terminal being connected to the third negative supply voltage and the negative terminal of the capacitor, and the positive terminal being connected to the positive terminal of the capacitor, the two low side drivers being powered by the third negative voltage supply, each of the high and low side switches having an open state and a closed state which state is controlled by the corresponding driver;

a control circuit connected to the first negative voltage supply and ground having output signals controlling the high and low side drivers to connect selectively the capacitor with a selected polarity to deliver a shock to said load; and a sense circuit connected to the second negative voltage supply and to ground to sense heartbeats.

23. The generator of claim 22 wherein the power supply further comprises first, second and third voltage regulators, connected to the battery, having respective first, second, and third outputs that are the first, second, and third negative voltage supplies.

24. The generator of claim 23 wherein the first voltage regulator has an output voltage between −1.0 and −3.0 volts, the second voltage regulator has an output voltage between −0.5 and −10.0 volts, and the third voltage regulator has an output between −10.0 and −15.0 volts.

25. The generator of claim 22 wherein the power supply further comprises a first circuit having an output voltage that is the first negative output supply, a second circuit having an output voltage that is the second negative output supply, and a third circuit having an output voltage that is the third negative output supply.

26. The generator of claim 25 wherein the first circuit further comprises a direct connection to the battery negative terminal.

27. The generator of claim 25 wherein the first circuit further comprises a voltage regulator.

28. The generator of claim 25 wherein the second circuit further comprises a direct connection to the battery negative terminal.

29. The generator of claim 25 wherein the second circuit further comprises a direct connection to the first negative voltage supply.

30. The generator of claim 25 wherein the second circuit further comprises a voltage regulator.

31. The generator of claim 25 wherein the second circuit further comprises a voltage multiplying circuit connected to the first negative voltage supply.

32. The generator of claim 25 wherein the third circuit further comprises a direct connection to the battery negative terminal.

33. The generator of claim 25 wherein the third circuit further comprises a direct connection to the first negative voltage supply.

34. The generator of claim 25 wherein the third circuit further comprises a voltage regulator.

35. The generator of claim 25 wherein the third circuit further comprises a voltage multiplying circuit connected to the first negative voltage supply.

36. The generator of claim 22 further comprising a sensing resistor interposed between the third negative supply voltage and the negative terminal of the shock delivery circuit.

37. The generator of claim 36 further comprising a voltage divider circuit connected to the positive terminal of the capacitor having a reference signal and an output corresponding to the capacitor output voltage.

38. The generator of claim 36 wherein the control circuit further comprises an input receiving a voltage signal corresponding to a voltage drop across the resistor and means for estimating the shock energy discharged during a shock based on sensing said voltage drop before and after said shock.

39. The generator of claim 22 further comprising a pace/sense circuit connected to the second negative voltage supply and ground to deliver pacing pulses and to sense heartbeats.

40. A method of controlling the delivery of shock energy to a load in an implantable defibrillator comprising:

providing a ground, providing a battery containing energy and having a positive terminal and a negative terminal;

connecting the battery positive terminal to ground;

providing a shock delivery circuit by connecting two high side switches to two low side switches in an H-bridge configuration having a positive terminal and a negative terminal and an output for delivering a shock to a load;

providing two isolated high side drivers for controlling respectively the high side switches and providing two low side drivers for controlling respectively the low side switches;

deriving from said battery a first negative voltage supply, a second negative voltage supply, and a third negative voltage supply;

connecting the third negative voltage supply to the negative terminal of the shock delivery circuit;

powering the two low side drivers between the third negative voltage supply and ground;

charging a capacitor with energy from the battery;

operating one of the two high side drivers and one of the two low side drivers to close the corresponding ones of said high and low side switches to discharge the capacitor across a load and delivering a shock with a first polarity for a first time, and thereafter opening said closed switches, said operating step comprising providing a logic signal having a logic high corresponding to ground and a logic low corresponding to the first negative voltage supply and delivering said logic high signal to said selected ones of the high and low side drivers to operate said drivers; and delivering said logic high signal to the other one of the two high side drivers and to the other one of the two low side drivers to close said corresponding high and low side switches to discharge the capacitor and delivering a shock across the load with a second polarity for a second time, and thereafter opening said closed switches.

41. The method of claim 40 wherein deriving said first, second, and third negative voltage supplies further comprises providing the first negative voltage supply in a range of between −1.0 and −3.0 volts, providing the second negative voltage supply in a range of between −0.5 and −10.0 volts, and providing the third negative voltage supply in a range of between −10.0 and −15.0 volts.

42. The method of claim 40 further comprising providing pace/sense circuit for delivering pacing pulses and for sensing a heartbeat and powering the pace/sense circuit between the second negative voltage supply and ground.

43. The method of claim 40 further comprising monitoring a voltage corresponding to the capacitor output prior to and subsequent to a shock delivered to the load, determining the shock energy of said shock based on determining a difference between the square of the sensed voltage prior to the shock and the square of the sensed voltage subsequent to the shock.

\* \* \* \* \*